US008889914B2

(12) United States Patent
Orschel et al.

(10) Patent No.: US 8,889,914 B2
(45) Date of Patent: Nov. 18, 2014

(54) METHOD FOR PRODUCING ISOPHORONE

(75) Inventors: Matthias Orschel, Muenster (DE); Robert Jansen, Bottrop (DE); Martin Maier, Herne (DE); Gerda Grund, Coesfeld (DE); Markus Schwarz, Haltern am See (DE); Joerg-Joachim Nitz, Oberhausen (DE); Axel Hengstermann, Senden (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/990,602

(22) PCT Filed: Nov. 17, 2011

(86) PCT No.: PCT/EP2011/070377
§ 371 (c)(1),
(2), (4) Date: May 30, 2013

(87) PCT Pub. No.: WO2012/076314
PCT Pub. Date: Jun. 14, 2012

(65) Prior Publication Data
US 2013/0261343 A1 Oct. 3, 2013

(30) Foreign Application Priority Data
Dec. 8, 2010 (DE) .......................... 10 2010 062 587

(51) Int. Cl.
C07C 45/00 (2006.01)
C07C 45/85 (2006.01)
C07C 45/74 (2006.01)
C07C 45/82 (2006.01)
C07C 45/42 (2006.01)

(52) U.S. Cl.
CPC .................. *C07C 45/42* (2013.01); *C07C 45/85* (2013.01); *C07C 45/74* (2013.01); *C07C 45/82* (2013.01); *C07C 2101/16* (2013.01)
USPC .......................................... 568/347; 568/376

(58) Field of Classification Search
None
See application file for complete search history.

(56) References Cited

U.S. PATENT DOCUMENTS

| 3,337,423 | A | | 8/1967 | Schmitt et al. | |
|---|---|---|---|---|---|
| 3,337,632 | A | * | 8/1967 | Baron et al. | 568/350 |
| 3,337,633 | A | | 8/1967 | Schmitt et al. | |
| 4,476,324 | A | | 10/1984 | Reichle | |
| 5,627,303 | A | * | 5/1997 | Braithwaite et al. | 568/388 |
| 2009/0048466 | A1 | | 2/2009 | Lettmann et al. | |
| 2010/0041921 | A1 | | 2/2010 | Lettmann et al. | |
| 2010/0261237 | A1 | | 10/2010 | Verseck et al. | |
| 2012/0101304 | A1 | | 4/2012 | Becker et al. | |

FOREIGN PATENT DOCUMENTS

| CN | 101633610 | | 1/2010 |
|---|---|---|---|
| EP | 0 095 783 | | 12/1983 |
| JP | 09169687 | A * | 6/1997 |
| WO | WO 2008/107226 A1 | | 9/2008 |
| WO | WO 2012/076314 A1 | | 6/2012 |
| WO | WO 2012/076315 A1 | | 6/2012 |
| WO | WO 2012/076317 A1 | | 6/2012 |
| WO | WO 2012/156187 A1 | | 11/2012 |

OTHER PUBLICATIONS

International Search Report Issued Jan. 27, 2012 in PCT/EP11/70377 Filed Nov. 17, 2013.
U.S. Appl. No. 13/885,532, filed May 15, 2013, Lettmann, et al.
U.S. Appl. No. 13/991,718, filed Jun. 5, 2013, Galle, et al.
U.S. Appl. No. 14/116,233, filed Nov. 7, 2013, Orschel, et al.
U.S. Appl. No. 14/124,449, filed Dec. 6, 2013, Schwarz, et al.
U.S. Appl. No. 14/124,486, filed Dec. 6, 2013, Nitz, et al.

* cited by examiner

*Primary Examiner* — Sudhakar Katakam

(57) ABSTRACT

The invention relates to a method for producing isophorone by catalyzed aldol condensation of acetone as an educt, reprocessing the reaction product, hydrolyzing the product stream, and separating into an organic and an aqueous fraction, obtaining isophorone from the organic fraction, distillatively reprocessing the aqueous fraction, and feeding the vapors from the head of the distillative reprocessing apparatus into the hydrolysis apparatus.

34 Claims, No Drawings

METHOD FOR PRODUCING ISOPHORONE

The invention relates to a process for preparing isophorone (3,5,5-trimethyl-2-cyclohexen-1-one).

Isophorone is used inter alia as a high-boiling solvent in the coatings industry, printing inks industry, adhesives industry and crop protection industry. According to the known prior art, the isophorone can be processed further, for example to give isophoronenitrile, isophoronediamine, isophorone diisocyanate or ketoisophorone.

Isophorone is the trimeric condensation product of acetone. Isophorone is prepared via a catalysed aldol condensation of acetone.

Both the existing patent literature and the scientific publications for preparing isophorone can be divided essentially into two areas. A distinction is drawn between liquid phase and gas phase processes. CN 101633610A also describes the condensation reaction for preparation of isophorone with supercritical acetone.

While mainly heterogeneous solid catalysts are employed in the gas phase processes described, both homogeneous and heterogeneous catalyst systems are used in liquid phase processes.

The reaction in the liquid phase is described in the patent literature virtually exclusively under alkaline conditions at elevated temperatures and high pressures.

In the field of isophorone chemistry, several patents to the Shell Development Company are known (U.S. Pat. No. 2,351,352, U.S. Pat. No. 2,344,226, U.S. Pat. No. 2,399,976, U.S. Pat. No. 2,419,051). U.S. Pat. No. 2,399,976 describes inter alia a condensation process for preparation of isophorone in a circulation reactor by means of alkali catalysis. In the process, the alkali used is recycled back into the reactor after phase separation, while the water of reaction formed is removed from the reactor circuit with the organic phase.

In addition, U.S. Pat. No. 2,419,051 describes a process in which hydrolysis of the higher condensation products can reverse the condensation of some of the autocondensates. The hydrolysis is performed in a pressure reactor at temperatures between 130-235° C. with an elevated alkali concentration.

In order to prevent phase separation in the synthesis, and hence to achieve a monophasic reaction regime, the applications of the Societe Industrielle Des Derivatives De L'Acetylene (DE 10 58 047, GB733650) describe alcohols as solubilizers. This process leads to a shorter reaction time. It is additionally stated there that the recycling of removed by-products into the reaction zone of the reactor enhances the selectivity of isophorone formation.

In the patent documents of Hibernia Chemie (DE 10 95 818, DE 11 44 269, DE 12 05 525, DE 11 65 018) from the 1960s, not only the use of a monophasic reactant/catalyst mixture with low alkali concentrations but also workup by means of a hydrolysis column is described. Isophorone is prepared here in a pressure reactor by condensation of acetone in the liquid phase by means of amounts of alkali (NaOH or KOH) of less than 1% as a catalyst and using amounts of water of less than 20% at temperatures of 150-250° C. The two phases which form in the reaction are emulsified both by a suitable reaction regime (reactor construction, pulse generator) and by the use of an emulsifier in order to achieve good contact between catalyst and the reactants (DE 10 95 818).

In addition, DE 12 05 525 describes the workup of by-products, called overcondensates. At 120-300° C., the hydrolysis of the overcondensates takes place with an aqueous alkali solution in what is called a pressure distillation column with constant removal of the acetone formed.

Pure isophorone is obtained from isophorone-containing condensation products by a removal of the low boilers by distillation under the same pressure at which the condensation is performed and by a further workup of the overcondensates still existing by distillation under reduced pressure (DE 11 44 269).

According to the application of BP Chemicals, use of potassium hydroxide solution (KOH) instead of the catalyst which is otherwise customary, sodium hydroxide solution (NaOH), can enhance the isophorone yield by up to 7% with constant selectivity (DE 25 20 681).

It has also been stated that the product quality of the isophorone can be increased by discharging coloured substances from the reaction column in a sidestream, and purifying this stream by distillation and acidic reaction (DE 26 45 281).

There also exist applications regarding isophorone preparation from Daicel Chemical Industries (JP 8245485, JP 8245486) from the 1990s. These state that reduction of the water concentration in the reactant stream, and also recycling of the aqueous alkali phase after phase separation into the hydrolysis section of the reactive distillation, can enhance the isophorone conversion.

As well as the liquid phase processes by means of homogeneous catalyst systems mentioned so far, there is also a patent publication involving heterogeneous catalyst systems in the liquid phase.

Thus, Elf Atochem S. A. in U.S. Pat. No. 5,849,957 describes the use of hydrotalcites ($Mg_{1-x}Al_xO_{1+x}$) as a heterogeneous catalyst system for the preparation of isophorone. In batchwise stirred tank experiments, it was possible with such a catalyst to achieve an acetone conversion of 38% and a selectivity for isophorone of 51%.

The preparation of isophorone by means of heterogeneous catalysts in the gas phase is also described frequently in the prior art.

The documents of Union Carbide (U.S. Pat. No. 4,086,188, U.S. Pat. No. 4,165,339, EP 095 783) describe the preparation of isophorone by means of lithium- or zinc-doped hydrotalcite-type precipitation catalysts. These catalysts can achieve, at an acetone conversion of 24%, a selectivity of 47% for isophorone (U.S. Pat. No. 4,086,188), and the catalyst can be fully regenerated by burning off the coking residues (U.S. Pat. No. 4,165,339). By optimizing the preparation conditions, the service life of such a catalyst can be increased to up to approx. 1000 hours (EP 095 783).

The patents of Aristech Chemical Corporation (WO9012645, WO9507255) describe various oxidic magnesium/aluminium catalysts which are prepared by slurrying of pseudoboehmite and magnesium oxide (WO 9012645). At an acetone conversion of 30%, the selectivity for isophorone is 76%.

As well as the catalysts, Aristech Chemical Company also describes a process for preparing isophorone in the gas phase in a fixed bed reactor (WO 95072559). The acetone conversion is limited here to 10-35% in order to minimize the formation of coking residues.

There is also a series of applications (JP 9059204, JP 9151152, JP 9151153, JP 9157207, JP 9157208, JP 9169687, JP 9169688) from Mitsui Toatsu Chemicals, which claim various zeolite and magnesium/alkali metal catalysts for the preparation of isophorone.

Scientific publications likewise describe, as well as the catalyst systems already mentioned in the patents, the use of carbon nanotubes as a catalyst for the isophorone synthesis. M. G. Stevens (Chem. Commun. 3, 1999) achieves, with caesium-doped carbon nanotubes, an acetone conversion of 11.9% at an isophorone selectivity of 61%.

The synthesis of isophorone forms a whole series of unwanted by-products. These are, for example, diacetone alcohol, mesityl oxide, phorone, mesitylene and a series of higher condensation products (overcondensates) of acetone (e.g. xylitones and isoxylitones). For this reason, the achievement of high yields and selectivities for isophorone is difficult to attain.

It was therefore a technical object of this invention to find a process which enables an increase in the economic viability of isophorone preparation. At the same time, ecological aspects should also be taken into account.

The invention provides a process for preparing isophorone by
catalysed aldol condensations with acetone as a reactant,
workup of the reaction product,
hydrolysis of the stream of value and separation into an organic fraction and an aqueous fraction,
obtaining isophorone from the organic fraction,
distillative workup of the aqueous fraction and passing the vapours from the top of the distillative workup apparatus onward into the hydrolysis apparatus.

The invention further provides a process for preparing isophorone wherein
the water from the bottoms of the distillative workup of the aqueous fraction is subjected to a flash evaporation and the purified water which forms is recycled into the process for preparing isophorone.

The inventive process can be performed continuously, batchwise or semicontinuously. However, it is preferably performed continuously.

Isophorone is prepared via catalysed aldol condensations with acetone as the reactant. In the first step, two acetone molecules react via the diacetone alcohol intermediate with elimination of water to form mesityl oxide. In a further reaction the mesityl oxide reacts with a further acetone, again with elimination of water, to form isophorone.

Isophorone is thus the reaction product of a condensation of three molecules of acetone with the elimination of two molecules of water.

As a consequence of the chemical similarity of the reactant used (acetone) and the intermediates/products formed, the isophorone synthesis does not proceed particularly selectively. Due to the multitude of competing aldol condensation reactions, under reaction conditions, not only is the desired isophorone target molecule obtained, but also a whole series of unwanted (higher) condensation products (e.g. xylitones and isoxylitones), and also further secondary components (e.g. mesitylene).

The isophorone synthesis is thus characterized by a complex reaction network; the selectivity is highly dependent on the conversion. In order to minimize the formation of unwanted (higher) condensation products, the acetone conversion has to be limited. Particularly in the gas phase reaction, the catalyst used can be deactivated by coking residues which form.

It has been found that the reaction mixture which forms can be worked up by the inventive process in a particularly economically viable and ecologically favourable manner to give isophorone.

The condensation reaction of acetone to isophorone (reaction) is preferably performed in a catalysed liquid phase reaction. Alternatively, isophorone can also be prepared by means of a gas phase reaction, or else by reaction in subcritical acetone.

For the performance of the reaction in accordance with the process according to the invention in the liquid phase, the acetone is converted to isophorone within the reactor used by catalytic reaction at temperatures in the range from 100 to 250° C., preferably 150-250° C. and more preferably 180-250° C., and a pressure range of 5 to 50 bar, preferably 10-50 bar and more preferably of 20-50 bar, it being possible to combine the values specified as desired.

For the performance of the reaction in accordance with the process according to the invention in the gas phase, the acetone is converted to isophorone within the reactor used by catalytic reaction at temperatures in the range from 100 to 400° C. and preferably 200-400° C.

For the performance of the reaction in accordance with the process according to the invention in the supercritical range, the acetone is converted to isophorone within the reactor used by catalytic reaction at temperatures in the range from 250 to 350° C. and a pressure range of 50 to 200 bar.

The catalytic reaction can be performed with the catalysts specified in the prior art, and the catalyst may be either a homogeneous or a heterogeneous catalyst. In the liquid phase, preference is given to using a homogeneous catalyst, and in the gas phase preference is given to using a heterogeneous catalyst. For the reaction in the supercritical range, it is possible to use either homogeneous or heterogeneous catalysts.

In the preferred reaction in the liquid phase, isophorone can be prepared by means of a homogeneous catalyst with amounts of alkali (NaOH or KOH) of <1% by weight, preferably of <0.5% by weight, more preferably <0.2% by weight. More preferably, the catalyst used is NaOH in amounts of 0.015 to 0.05% by weight. The water concentration used is determined by factors including the recycle streams of the workup processes; it should, based on the total amount of liquid, be <40%, preferably <30%.

The reaction can be performed in any desired reactors according to the prior art, for example tubular reactors, stirred tanks, stirred tank cascades, fixed bed reactors, pressure distillation reactors or reactive distillations, microstructured reactors, loop reactors, etc., or in combinations of any desired reactors. The choice of reactors is not restricted to the selection mentioned.

The term "pressure distillation reactor" should be equated here with apparatuses in which a reactive distillation is performed. The reactive distillation has been sufficiently well described in the specialist literature, for example in Ullmann's Encylcopedia of Industrial Chemistry (M. Sakuth, D. Reusch, R. Janowsky: Reactive Distillation© 2008 Wiley-VCH Verlag GmbH & Co KGaA, Weinheim, DOI: 10.1002/14356007.c22_c01.pub2). Here and in the literature cited, all standard processes and apparatuses for reactive distillation are described. If the term "reactive distillation column" is used in the following text of the patent specification, what is meant is all embodiments of reactive distillation as described in the literature.

In a preferred version, the reaction is conducted in reactive distillation columns, tubular reactors or fixed bed reactors. Particular preference is given to tubular reactors.

After performing the reaction, the reaction mixture is worked up and separated into the individual components. These are, as well as isophorone, what are called low boilers, for example acetone, diacetone alcohol and mesityl oxide, and also a series of higher condensation products (overcondensates) of acetone (e.g. xylitones and isoxylitones) and water, with or without catalyst. The separation is performed in full or in part.

The removal of the individual fractions can be performed by all separation methods, for example distillation, flash evaporation, crystallization, extraction, sorption, permeation, phase separation or combinations of the above, continuously or batchwise, in one or more stages. Preference is given to achieving separation by distillation in one or more apparatuses. The distillation can be performed spatially separately from the isophorone synthesis (reaction) or take place in one apparatus. Preferably, the individual fractions are removed by a reactive distillation, preferably in a reactive distillation column.

Particular preference is given to performing the removal spatially separately from the isophorone synthesis (reaction) in a reactive distillation column with a sidestream withdrawal.

Preferably, the removal is effected in three fractions:
a) A fraction composed of unconverted acetone, water and low boilers, for example diacetone alcohol and mesityl oxide, which is condensed and then recycled into the reactor for reaction.
b) A fraction in which coloured substances in particular are enriched. This fraction is purified further and the materials of value present are recycled into the process.
c) A fraction composed particularly of isophorone, more highly condensed products and water, with or without catalyst, called material of value stream. This fraction is subsequently subjected to a hydrolysis.

In the preferred embodiment, fraction a) is withdrawn as a vapour stream comprising essentially acetone, water and low boilers, essentially diacetone alcohol and mesityl oxide, condensed and added again to the reactor with the acetone, water and optionally catalyst feedstocks. In the preferred embodiment, fraction b) is withdrawn as a sidestream of the distillation column, preferably of a reactive distillation column, optionally neutralized and worked up further. In the workup, it is possible to use all standard separation methods, for example distillation, flash evaporation, crystallization, extraction, sorption, permeation, phase separation, or combinations of the above. The purification can be performed continuously or batchwise, in one or more stages. The purification is preferably achieved by distillation. The purification is more preferably achieved by a combination of neutralization or extraction and subsequent distillation, preferably in a reactive distillation column. The worked-up phase is preferably conducted into the hydrolysis with the products of value composed of isophorone and high boilers, with or without catalyst. Any further phase obtained, composed of products of value essentially comprising acetone, diacetone alcohol and mesityl oxide, is preferably recycled into the reaction. Any residues obtained are sent to thermal utilization.

Fraction c) is subjected to a hydrolysis. The aim of the hydrolysis is to convert by-products partly or fully to isophorone, acetone and other products of value. The hydrolysis can be performed in all standard reactors, which have already been described above, or distillation columns or combinations of the two. Preference is given to performing the hydrolysis by a reactive distillation, in which the low boilers formed, essentially comprising acetone, diacetone alcohol and mesityl oxide, are removed directly from the hydrolysis zone and recycled into the reaction, and are thus no longer available for side reactions in the hydrolysis.

Most preferably, the hydrolysis of fraction c) is performed in an apparatus, a reactive distillation, preferably in a reactive distillation column, with simultaneous separation of the reaction mixture into fractions a) to c), such that the products formed are correspondingly separated at the same time as fraction c) is hydrolyzed.

Optionally, the hydrolysis and the distillative removal can also take place in an apparatus with the isophorone synthesis (reaction).

The hydrolysis can be performed in all mixing ratios of the organic components with water, with or without catalyst. The water concentration in the hydrolysis is 0.1-99.9% by weight, preferably 30-90% by weight. In the case of homogeneous catalysis, the catalyst used in the hydrolysis is preferably that which is also used in the reaction section. Preference is given to catalyst concentrations of 0.001-10% by weight, more preferably of 0.05-1% by weight. The pressure in the hydrolysis reactor is 1-200 bar, preferably 20-60 bar; more preferably, the hydrolysis is performed at least at the pressure which also exists in the isophorone synthesis step (reaction). The hydrolysis temperature is 100-300° C., preferably 210-260° C. More preferably in the case of use of a reactive distillation column, a temperature or temperature profile will be established according to the boiling temperatures in the bottoms and at the individual separation or reaction stages.

The hydrolysis can be performed in one or more apparatuses, in one stage or multiple stages.

Fraction c) which has thus been worked up is subsequently removed from the hydrolysis reactor or reactive distillative column, cooled and subjected to a phase separation.

The phase separation is effected to give an essentially organic fraction d) and an essentially aqueous fraction e), which, in the case of homogeneous catalysis, also comprises the catalyst. It is possible to use customary phase separation vessels with and without internals. The phase separation is effected at a temperature between 0-200° C., preferably at 0-100° C. and more preferably at 20-70° C., and a pressure of 1-150 bar and preferably 20-60 bar, more preferably at the pressure which also exists in the hydrolysis.

The essentially organic fraction d), comprising the isophorone target product, is optionally neutralized and purified by customary methods, so as to obtain an isophorone with the desired purity and colour stability. It is possible here to use all standard separation methods, for example distillation, flash evaporation, crystallization, extraction, sorption, permeation, phase separation or combinations of the above. The purification can be performed continuously or batchwise, in one or more stages, under pressure or under reduced pressure. The purification is preferably achieved by distillation. The purification is more preferably achieved by a combination of neutralization or extraction and subsequent distillation.

At this point, the distillative workup of the aqueous fraction e) (wastewater cleaning) and conduction of the vapours from the top of the distillative workup apparatus into the hydrolysis apparatus will be described in detail.

The essentially aqueous fraction e) is supplied to a wastewater cleaning operation. This involves the separation of the water of reaction as the main constituent, with or without the catalyst, from any undissolved organic components, for example isophorone, acetone and more highly condensed products. The wastewater cleaning operation is preferably performed in one or more distillation columns.

It is essential to the invention that the vapours of the wastewater column are passed directly into the apparatus in which the hydrolysis takes place. This simultaneously solves several problems in the current prior art:
1) Since the vapours consist essentially of water, a necessary sufficiently high water concentration is established in the hydrolysis section, such that no additional fresh water need be introduced into the hydrolysis.
2) The organic components dissolved in fraction e) are recycled partially or completely into the process via the vapours of the wastewater column. This minimizes organic contamination in the wastewater and, since the contamination is essentially isophorone, increases the overall yield in the process. This novel connection of the wastewater column thus makes a significant contribution to the ecological and economic process regime.

3) Moreover, the necessary heat for the hydrolysis or the distillative separation of the reaction mixture is provided by the vapours; no separate heating is required.

The pressure in the wastewater column is 1-200 bar, preferably 20-60 bar. Particular preference is given to working at the system pressure which is established in the overall hydrolysis/wastewater column system when the vapours of the wastewater column are passed directly into the hydrolysis section of the reactive distillation. The temperature in the wastewater column corresponds to the boiling temperature of fraction e) under the pressure conditions. The preferred temperature of the vapours is 200-300° C.

There follows a detailed description of how the water from the bottom of the distillative workup of the aqueous fraction is subjected to a flash evaporation and the cleaned water formed is recycled into the process for preparation of isophorone.

The wastewater obtained in the bottom of the wastewater column (stream f) can be cooled and discarded. Preferably, the wastewater f), however, is sent to a flash evaporation and thus separated further. The vapours g) of the flash evaporation stage, which consist essentially of pure water, can be condensed and recycled as water into the process, preferably into the reaction, for example for dilution of the catalyst used (in the case of homogeneous catalysis). This once again reduces the amount of wastewater. The flash evaporation can be performed in one or more stages, continuously or batchwise. The pressure in the flash evaporation is in any case below the pressure in the wastewater column. In the process according to the invention, preference is given to the use of a flash evaporation.

All distillation and reaction steps in the process can be performed in reactors or apparatuses with or without internals, for example dephlegmators, unordered internals or random packagings, ordered internals or structured packings, trays with or without forced flow.

All metallic materials which are in contact with the product and are used for the reaction, and the apparatuses produced from the metallic materials and the internals thereof, must be stable to alkalis. Depending on the risk, different stability requirements may exist. For the stabilities, not only the chemical and/or mechanical properties are of significance, but also the methods of manufacture employed and the assessment standards during the testing.

For the metallic materials, reference is made in some cases to the AD 2000-Merkblatt HP 0, November 2008 edition (General Principles of Design, Manufacture and Associated Tests) and DIN EN 10020, July 2000 edition (Determination and Classification of Grades of Steel). The material groups named therein are cited to specify the designations (e.g. "austenitic stainless steel"). If meaningful in a technical sense, the statements apply to all industrially available variants of the materials (for example forged variants, rolled variants and cast variants) with comparable stability to alkali corrosion.

a) For pressure-bearing components in contact with product, any materials suitable according to the prior art can be employed, for example:
Heat-resistant steels (e.g. material subgroups 5.1 to 5.4 and 6.1 to 6.4 according to AD 2000 HP 0)
Austenitic stainless steels (e.g. material subgroups 8.1 to 8.2 according to AD 2000 HP 0)
Ferrite-free austenitic stainless steels (e.g. material subgroups 8.1 to 8.2 according to AD 2000 HP 0)
Ferritic-austenitic stainless steels (e.g. material subgroups 10.1 to 10.2 according to AD 2000 HP 0)
Nickel and nickel alloys (e.g. material subgroups 41 to 46 according to AD 2000 HP 0)

It is also possible to employ combinations of the above-mentioned materials. In this case, the choice of materials is not restricted to the selection mentioned and also includes equivalent or higher-quality variants in terms of corrosion. Preference is given to materials which, according to the prior art, taking account of the stress conditions and risks, feature industrial stability to alkalis. It is not possible to dispense with heat treatments if this impermissibly alters the technical stability to alkalis.

b) For non-pressure-bearing components in contact with product, any materials suitable according to the prior art can be employed, for example:
All materials mentioned under a)
Unalloyed steels (e.g. material subgroups 1.1 to 1.2 according to AD 2000 HP 0)
Unalloyed steels and other alloyed steels (e.g. according to DIN EN 10020)

It is also possible to employ combinations of the above-mentioned materials. In this case, the choice of materials is not restricted to the selection mentioned and also includes equivalent or higher-quality variants in terms of corrosion. Preference is given to materials which, according to the prior art, taking account of the stress conditions and risks, feature sufficient stability to alkalis. For non-pressure-bearing components, it may be possible to accept temporary stabilities depending on the risk. It is not possible to dispense with heat treatments if this impermissibly alters the technical stability to alkalis.

c) The material properties are altered by suitable manufacturing processes which are described hereinafter according to the designations given in DIN 8580, September 2003 edition (manufacturing processes—terms and definitions, division). The following manufacturing processes can be employed, for example, for the processing of the metallic materials:
Primary shaping (e.g. casting)
Reshaping (e.g. cold forming and hot forming)
Separating (e.g. machining with geometrically defined blade and machining with geometrically undefined blade)
Joining (e.g. fusion welding)
Coating (e.g. coating from the liquid state, melt dipping, plating, thermal spraying, sintering, electrocoating, chemical coating and coating from the gaseous and vaporous state)
Manufacturing processes which alter material properties (consolidation by reshaping, for example forging, rolling, blasting; heat treatment, for example tempering, recrystallization annealing, low-voltage annealing, normalization annealing; thermomechanical treatments, for example the combination of heat treatment and forming treatment; sintering and firing).

It is also possible to employ combinations of the above-mentioned manufacturing processes. In this case, the choice of manufacturing processes is not restricted to the selection mentioned. Preference is given to processes which, according to the prior art, ensure the required alkali stability of the respective materials and apparatuses.

d) The following tests on apparatuses and internals, and more particularly on the weld bonds thereof, for example, can be employed:
Magnet particle testing MT
Penetration testing PT
Radiographic testing RT Ultrasound testing UT
Visual testing VT
Hardness testing HT
Alloy analysis Combinations of the abovementioned test methods are also possible. In this case, the choice of test methods is not restricted to the selection mentioned. Preference is given to test methods and assessment principles which, according to the prior art, contribute to ensuring the required alkali stability of the respective components.

EXAMPLE, INVENTIVE

A crude isophorone mixture consisting of isophorone, lower-boiling components, higher-boiling components, and also water and catalyst, which has been obtained by one of the procedures described above, is withdrawn from the hydrolysis apparatus, cooled to approx. 40-60° C. and subjected to a phase separation. The phase ratio is 1 part of organic phase, 4 parts of aqueous phase. In the aqueous phase, 1% by weight of isophorone is accordingly still present, corresponding to about 4% by weight of the organic phase. In the subsequent wastewater distillation, the isophorone content is vaporized virtually completely and the water to an extent of 75% by weight, and passed into the hydrolysis apparatus.

In the course of cooling of the bottoms from the wastewater column by flash evaporation, a further 25% by weight of the water is recovered.

Calculation for 1 tonne of isophorone production: 4% by weight (approx. 40 kg) of additional isophorone production, minimization of wastewater volume, low organic contamination of the wastewater.

COMPARISON, NONINVENTIVE

Comparison with the conventional process: approx. 4% by weight of isophorone loss via the wastewater, based on 1 tonne of isophorone production. The additional requirement for water corresponds to 5 times the volume, based on 1 tonne of isophorone production. The wastewater volume is likewise 5 times higher, based on 1 tonne of isophorone production.

The invention claimed is:

1. A process for preparing isophorone, the process comprising:
    (i) reacting acetone via a catalysed aldol condensation in a reactor, thereby obtaining a reaction product,
    (ii) working-up the reaction product, thereby obtaining a stream of value,
    (iii) hydrolyzing the stream of value in a hydrolysis apparatus,
    (iv) separating the stream of value into an organic fraction and an aqueous fraction,
    (v) recovering isophorone from the organic fraction,
    (vi) distilling the aqueous fraction in a distillative workup apparatus comprising a top and a bottom,
    (vii) passing vapours from the top of the distillative workup apparatus onward into the hydrolysis apparatus, and
    (viii) subjecting water from the bottom of the distillative workup apparatus to a flash evaporation, thereby obtaining purified water which is recycled into the reactor for preparing isophorone.

2. The process according to claim 1, wherein the catalysed aldol condensation is performed in a liquid phase at a temperature of from 100 to 250° C., and a pressure of from 5 to 50 bar.

3. The process according to claim 1, wherein the catalysed aldol condensation is performed in a gas phase at a temperature of from 100 to 400° C.

4. The process according to claim 1, wherein the catalysed aldol condensation is performed in a supercritical range at a temperature of from 250 to 350° C. and a pressure of from 50 to 200 bar.

5. The process according to claim 1, wherein a homogeneous or a heterogeneous catalyst is used in the catalysed aldol condensation.

6. The process according to claim 1, wherein the catalysed aldol condensation occurs in a liquid phase with a homogeneous catalyst.

7. The process according to claim 6, wherein the homogeneous catalyst is alkali of <1% by weight.

8. The process according to claim 1, wherein the catalysed aldol condensation is performed in at least one reactor selected from the group consisting of a tubular reactor, a stirred tank, a stirred tank cascade, a fixed bed reactor, a reactive distillation column, a microstructured reactor, and a loop reactor.

9. The process according to claim 1, wherein the catalysed aldol condensation is performed in a reactive distillation column, a tubular reactor or a fixed bed reactor.

10. The process according to claim 1, wherein said working-up (ii) comprises (ix) separating the reaction product into individual components and removing the individual components in full or in part.

11. The process according to claim 10, wherein the individual components are removed by at least one separation method selected from the group consisting of distillation, flash evaporation, crystallization, extraction, sorption, permeation, and phase separation, continuously or batchwise, in one or more stages.

12. The process according to claim 1, wherein said distilling (vi) is performed spatially separately from the catalysed aldol condensation or takes place in a reaction apparatus.

13. The process according to claim 10, wherein the individual components are removed via a reactive distillation spatially separately from the catalysed aldol condensation.

14. The process according to claim 10, wherein the individual components are removed in three fractions:
    a) a fraction comprising unconverted acetone, water and low boilers, wherein the fraction a) is condensed and then recycled into the reactor;
    b) a fraction comprising enriched coloured substances, wherein the fraction b) is purified further and materials of value are recycled into the reactor; and
    c) a fraction comprising isophorone, more highly condensed products, water, and catalyst, wherein the fraction c) is subsequently subjected to a hydrolysis.

15. The process according to claim 14, wherein the fraction a) is withdrawn as a vapour stream comprising acetone, water, and low boilers comprising diacetone alcohol and mesityl oxide, condensed and added again to the reactor with a feedstock comprising acetone, water, and catalyst.

16. The process according to claim 14, wherein the fraction b) is withdrawn as a sidestream of a distillation column.

17. The process according to claim 14, wherein the fraction b) is purified by a combination of neutralization or extraction and subsequent distillation in a reactive distillation column, thereby obtaining a worked-up phase.

18. The process according to claim 17, wherein the worked-up phase of the fraction b) is conducted into the hydrolysis apparatus with products of value comprising isophorone and high boilers, with or without catalyst.

19. The process according to claim 17, wherein any further phase of the fraction b) comprises acetone, diacetone alcohol and mesityl oxide, and is recycled into the reactor.

20. The process according to claim 14, wherein the fraction c) is subjected to the hydrolysis in which by-products are converted partly or fully to isophorone, acetone and other products of value.

21. The process according to claim 1, wherein said hydrolyzing (iii) is performed in a reactive distillation column in which low boilers comprising acetone, diacetone alcohol and mesityl oxide are obtained and recycled into the reactor.

22. The process according to claim 14, wherein the hydrolysis of the fraction c) is performed in an apparatus via a reactive distillation with a simultaneous separation of the reaction product into the fractions a), b), and c).

23. The process according to claim 14, wherein the hydrolysis of the fraction c) is effected at a water concentration of 0.1-99.9% by weight.

24. The process according to claim 14, wherein the hydrolysis of the fraction c) is effected at a catalyst concentration of 0.001-10% by weight.

25. The process according to claim 14, wherein the hydrolysis of the fraction c) is performed at a pressure of 1-200 bar.

26. The process according to claim 14, wherein the hydrolysis of the fraction c) is effected at a temperature of 100-300° C.

27. The process according to claim 14, wherein the hydrolysis of the fraction c) is performed in a reactive distillation column at a temperature or a temperature profile established according to boiling temperatures in bottoms and at individual separation or reaction stages.

28. The process according to claim 14, wherein the fraction c) is separated into an organic fraction d) and an aqueous fraction e).

29. The process according to claim 28, wherein the organic fraction d) is purified by distillation.

30. The process according to claim 28, wherein the aqueous fraction e) is supplied to a wastewater cleaning operation, which optionally is performed in one or more distillation columns.

31. The process according to claim 30, wherein the wastewater cleaning operation is performed at a pressure of 1-200 bar.

32. The process according to claim 30, wherein the wastewater cleaning operation is effected at a system pressure established in an overall hydrolysis/wastewater column system.

33. The process according to claim 30, wherein a pressure in the flash evaporation is below a pressure in the wastewater column.

34. The process according to claim 33, wherein vapours g) obtained from the flash evaporation consist essentially of pure water and are condensed and recycled as water into the reactor.

* * * * *